United States Patent [19]

Denty et al.

[11] 4,402,687

[45] Sep. 6, 1983

[54] SUCTION COLLECTION SYSTEM

[76] Inventors: Stephen C. Denty, 550 Cooper Ctr. W., Pennsauken, N.J. 08109; John Meserko, 5523 Hudson Dr., Hudson, Ohio 44236

[21] Appl. No.: 364,874

[22] Filed: Apr. 2, 1982

[51] Int. Cl.[3] .............................................. A61M 1/00

[52] U.S. Cl. .................................... 604/319; 215/246

[58] Field of Search .................. 604/4, 5, 6, 317, 318, 604/319, 320, 323, 324, 326, 327, 405, 406; 215/246; 206/497, 524.8; 220/449; 210/416.1; 128/760, 767; 137/205; 433/91

[56] References Cited

U.S. PATENT DOCUMENTS

| | | | |
|---|---|---|---|
| 2,913,120 | 11/1959 | Glasby, Jr. | 210/416.1 |
| 3,605,786 | 9/1971 | Machin, Jr. | 137/205 |
| 3,690,315 | 9/1972 | Chittenden et al. | 604/324 |
| 3,833,001 | 9/1974 | Abrahams | 604/319 |
| 4,018,904 | 4/1977 | Muraoka | 215/246 |
| 4,306,557 | 12/1981 | North | 604/319 |

*Primary Examiner*—Richard J. Apley
*Assistant Examiner*—J. L. Kruter
*Attorney, Agent, or Firm*—Duffield & Lehrer

[57] ABSTRACT

A suction collection system for use in collecting body fluids from a patient prior to, during or after surgery includes a rigid, cylindrically shaped hollow canister having a cylindrical side wall and disc-shaped top and bottom walls. A thin flexible plastic sheet material covers the entire outer surface of the canister to form an airtight receptacle. A first port in the top wall is adapted to be connected to a vacuum source for reducing the pressure within the receptacle. A second port is adapted to be connected to an aspirator for collecting blood and other body fluids. Within the canister and connected to the second port is a gross filter for removing particles from the fluid before it passes into the receptacle. Fluid within the receptacle can be removed through a normally closed outlet port in the bottom wall of the canister.

3 Claims, 3 Drawing Figures

SUCTION COLLECTION SYSTEM

BACKGROUND OF THE INVENTION

The present invention is directed toward a suction collection system and more particularly toward such a system which may be used to collect a patient's own blood lost during surgery or for other fluid salvaging when indicated and to store the same in a sterile receptacle so that it may be readministered back to the patient intravenously.

Suction collection devices have been utilized for some time to collect blood or other body fluids and materials during surgery or when a patient is bleeding from a wound. This may be necessary so that a doctor can have a clear view of and access to the wound or area undergoing surgery.

Conventionally used suction collection receptacles normally include a substantially rigid canister or container with a flexible reservoir such as a bag comprised of polyvinyl chloride or the like suspended therein. A vacuum source is utilized to reduce the pressure within the container. A suction line leading from the container and having an aspirator or similar device attached to the end thereof is utilized to suction the blood from a patient. One such device is shown, for example, in U.S. Pat. No. 3,704,709.

These prior art devices have had several drawbacks. Firstly, some provide no means for reutilizing the blood or other fluid which has been collected. Furthermore, because a suction is being created within the canister, it is not impossible for the flexible bag to collapse or be drawn up toward the vacuum line.

Devices such as shown in U.S. Pat. No. 3,866,608 have been proposed to overcome the problems with the above-described prior art devices. This patent describes a system which includes a soft pliable bag within a canister which includes means for removing the fluid which had been collected in the bag. The bag is prevented from collapsing during suction by a second vacuum line which is connected to the interior of the canister and which reduces the pressure around the outer surface of the pliable bag. The system is, however, somewhat complex and requires various procedural steps to set up the canister and bag and to remove the bag therefrom when it is desired to utilize the blood, thus adding to the time and costs of the system.

SUMMARY OF THE INVENTION

The present invention is designed to overcome all of the defects in the prior devices known to Applicants and provides a receptable which is easy to utilize, inexpensive and, therefore, readily disposable and which does not suffer from the problem of an internal bag which may collapse. This is accomplished in accordance with the invention by a rigid, cylindrically shaped hollow canister having a cylindrical side wall and disc-shaped top and bottom walls. A thin flexible plastic sheet material covers the entire outer surface of the canister to form an airtight receptacle. A first port in the top wall is adapted to be connected to a vacuum source for reducing the pressure within the receptacle. A second port is adapted to be connected to an aspirator for collecting blood and other body fluids. Within the canister and connected to the second port is a gross filter for removing particles from the fluid before it passes into the receptacle. Fluid within the receptacle can be removed through a normally closed outlet port in the bottom wall of the canister.

BRIEF DESCRIPTION OF THE DRAWING

For the purpose of illustrating the invention, there is shown in the accompanying drawing one form which is presently preferred; it being understood that the invention is not intended to be limited to the precise arrangements and instrumentalities shown.

DETAILED DESCRIPTION OF THE PREFERRED EMBODIMENT

Figure 1:
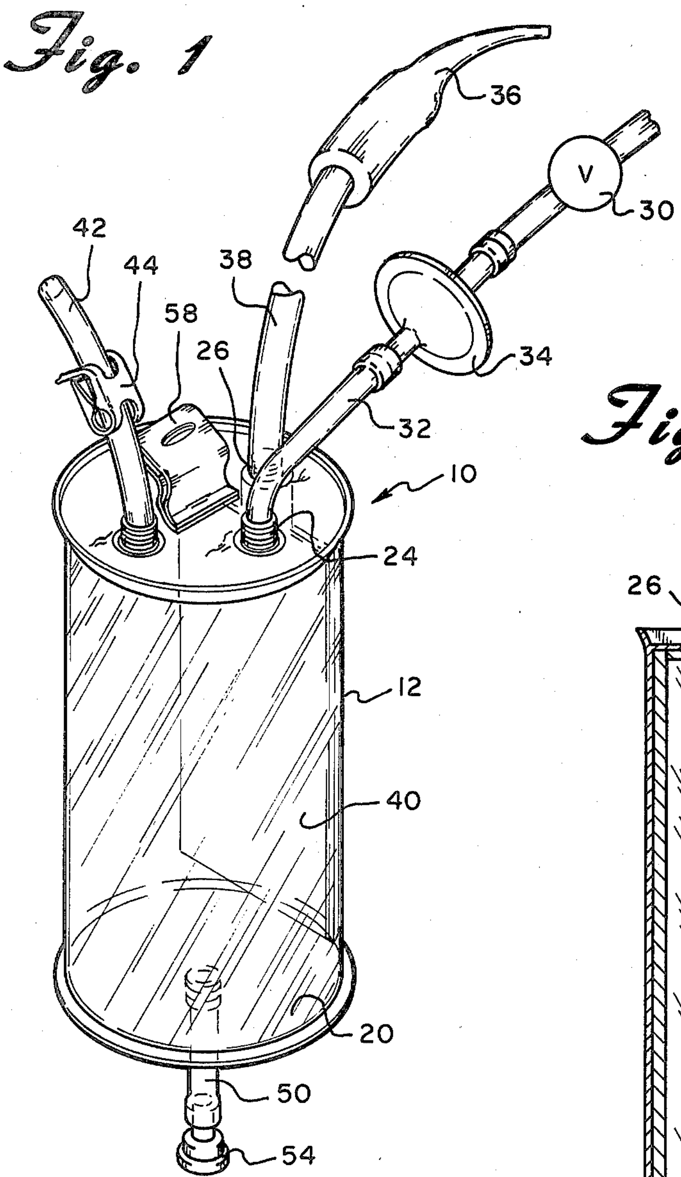
FIG. 1 is a perspective view of the suction collection system constructed in accordance with the principles of the present invention.
Figure 4:
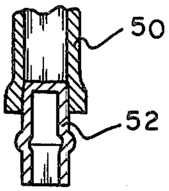
FIG. 4 is a sectional view taken through the line 4—4 of FIG. 2.

Referring now to the drawing in detail wherein like reference numerals have been used throughout the various figures to designate like elements, there is shown in FIG. 1 a perspective view of a suction collection system constructed in accordance with the principles of the present invention and designated generally as 10. The principal portion of the system 10 is the receptacle 12.

Figure 2:
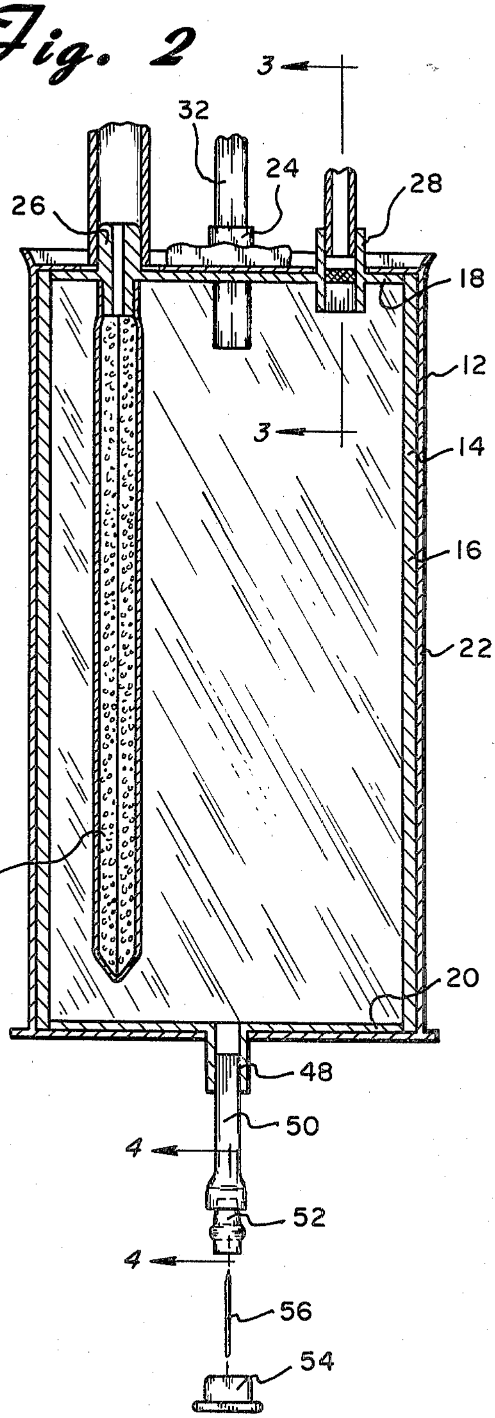
FIG. 2 is a cross-sectional view thereof.
Figure 3:
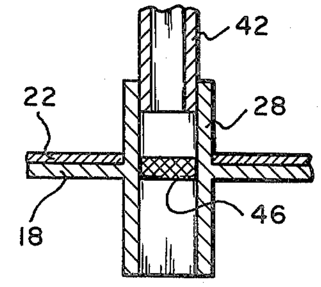
FIG. 3 is a sectional view taken through the line 3—3 of FIG. 2.

As shown most clearly in FIGS. 1 and 2, the receptacle 12 is constructed from a substantially rigid and substantially cylindrically shaped canister 14 having a cylindrical side wall 16, a disc-shaped top end wall 18 and a similar disc-shaped bottom end wall 20. The walls 16, 18 and 20 are preferably made from a clear plastic material. The end walls 18 and 20 are preferably secured to the cylindrical wall 16 although it is not necessary that there be an airtight seal therebetween.

A thin flexible plastic sheet material 22 covers the entire outer surface of the canister formed by the cylindrical wall 16 and end walls 18 and 20. The covering 22 is preferably transparent and may be comprised of polyvinyl chloride or some similar material. The covering 22 is also preferably heat shrunk around the canister 14. Similar to the canister 14, the covering 22 may be constructed of a cylindrical side wall and two end walls which are joined together. This covering, however, is totally airtight so as to make the interior of the canister an airtight receptacle.

Located in the top end of the receptacle 12 for providing communication between the exterior and the interior of the receptacle are a plurality of ports 24, 26 and 28. Port 24 is adapted to be connected to a vacuum source 30 through a length of plastic tubing 32 so that the pressure within the receptacle 12 can be reduced. A bacteria filter 34 is placed in the tubing line 32 so as to prevent bacteria or other harmful elements which may be in the receptacle from being drawn out into the vacuum source and also prevents contaminants which may be in the vacuum line from entering the receptacle.

An aspirator or similar device 36 for suctioning blood from a patient is connected to port 26 through a desired length of tubing 38. Located within the canister 14 and connected to the port 26 is a large surface area gross filter 40. Filter 40 removes particulate matter and debris from the fluid before it passes into the receptacle 12.

The third port 28 may be utilized to selectively allow air into the receptacle 12. This is done when it is desired to allow the contents of the receptacle to flow out through the bottom thereof as will be explained hereinafter. A short length of plastic tubing 42 is connected to the port 28 but is held closed by a clamp 44. Manipulating the clamp 44 or removing the same will allow air to freely pass through the tubing 42 into the receptacle. A bacteria filter 46 may be located within the port 28 so as to prevent bacteria from the atmosphere from entering the receptacle 12.

An outlet port 48 is located on the bottom wall of the receptacle 12 and provides further communication between the interior and exterior thereof. A length of tubing 50 carrying a blood spike receptacle 52 is connected to the outlet port 48. A cap 54 normally closes the blood spike receptacle 52. When it is desired to withdraw fluid from the interior of the receptacle 12, a conventional blood spike 56 with associated tubing is inserted into the blood spike receptacle 52.

The suction collection system 10 of the present invention is utilized in the following manner. When it is desired to remove blood or other fluid from a wound or during surgery, the vacuum source 30 is energized and with the clamp 44 and cap 54 in place, the aspirator 36 is positioned to suck up blood or other fluids. It should be readily apparent that a chest tube or similar other drainage device could be utilized in place of the aspirator 36. As the fluids pass through the tube 38, they are filtered by a filter 40 and the filtered fluid passes into the interior of the receptacle 12. When the receptacle 12 is full or after the procedure is completed, the vacuum source 30 is turned off and clamps are placed on the tube sections 32 and 38. The receptacle 12 which had been suspended by some appropriate support means by the use of tab 58 may then be disposed of or stored for later use. Alternatively, the fluid in the receptacle 12 may be autotransfused. That is, an intravenous line may be attached to the port 48 through the blood spike receptacle 52 and attached to the patient. Clamp 44 may then be opened so that, through gravity and air pressure, the fluid within the receptacle 12 will flow downwardly and to the patient.

The present invention may be embodied in other specific forms without departing from the spirit or essential attributes thereof and accordingly, reference should be made to the appended claims rather than to the foregoing specification as indicating the scope of the invention.

We claim:

1. A suction collection system comprising:

a rigid substantially cylindrically shaped canister including a cylindrical wall and top and bottom disc-shaped end walls;

a thin flexible plastic sheet material covering the entire outer surface of said canister so as to make an airtight receptacle;

first and second ports adjacent the top end of said canister and being adapted to provide communication between the exterior and the interior of said receptacle;

a vacuum source and means for connecting the same to said first port;

an aspirator means and means for connecting the same to said second port;

a filter within said receptacle and being connected to said second port whereby fluid from said aspirator passes through said second port and then through said filter into said receptacle;

a normally closed outlet port adjacent the bottom of said canister and being adapted to provide communication between the interior of said receptacle and the exterior thereof.

2. The suction collection system as claimed in claim 1 wherein said means for connecting said vacuum source to said first port includes a bacteria filter.

3. The suction collection system as claimed in claim 1 further including a third port adjacent the top of said canister, said third port being normally closed but including means for selectively opening the same for providing communication between the atmosphere and the interior of said receptacle.

* * * * *